US00PP21918P2

(12) United States Plant Patent
van Veen

(10) Patent No.: US PP21,918 P2
(45) Date of Patent: May 10, 2011

(54) ***ASTILBE* PLANT NAMED 'SPOTLIGHT'**

(50) Latin Name: *Astilbe hybrida*
Varietal Denomination: Spotlight

(75) Inventor: Wilhelmus Franciscus van Veen, Noorden (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 12/655,600

(22) Filed: Dec. 31, 2009

(51) Int. Cl.
*A01H 5/00* (2006.01)

(52) U.S. Cl. ..... Plt./407

(58) Field of Classification Search ..... Plt./407
See application file for complete search history.

(56) References Cited

OTHER PUBLICATIONS

UPOV-ROM GTITM, Plant Variety Database, 2010/06, GTI Jouve Retrieval Software, Citation for plant 'Spotlight'.*

* cited by examiner

*Primary Examiner* — Susan B McCormick Ewoldt
(74) *Attorney, Agent, or Firm* — C. A. Whealy

(57) ABSTRACT

A new and distinct cultivar of *Astilbe* plant named 'Spotlight', characterized by its upright and strong plant habit; dark-colored foliage; freely and uniformly flowering habit with inflorescences positioned above the foliar plane; light pink-colored flowers; long flowering period; and good garden performance.

2 Drawing Sheets

Botanical designation: *Astilbe hybrida.*
Cultivar denomination: 'SPOTLIGHT'.

BACKGROUND OF THE INVENTION

The present invention relates to a new and distinct cultivar of *Astilbe* plant, botanically known as *Astilbe hybrida* and hereinafter referred to by the name 'Spotlight'.

The new *Astilbe* plant is a product of a planned breeding program conducted by the Inventor in Noorden, The Netherlands. The objective of the breeding program was to create new long-flowering *Astilbe* plants with attractive foliage and flower coloration.

The new *Astilbe* plant originated from a cross-pollination made by the Inventor in 2003 in Noorden, The Netherlands, of an unnamed proprietary seedling selection of *Astilbe chinensis*×*Astilbe arendsii,* not patented, as the female, or seed, parent with *Astilbe arendsii* 'Weisse Gloria', not patented, as the male, or pollen, parent. The new *Astilbe* plant was discovered and selected by the Inventor as a single flowering plant within the progeny of the stated cross-pollination in a controlled greenhouse environment in Noorden, The Netherlands in 2005.

Asexual reproduction of the new *Astilbe* plant by divisions in a controlled environment in Noorden, The Netherlands since January, 2006, has shown that the unique features of this new *Astilbe* plant are stable and reproduced true to type in successive generations.

SUMMARY OF THE INVENTION

Plants of the new *Astilbe* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Spotlight'. These characteristics in combination distinguish 'Spotlight' as a new and distinct cultivar of *Astilbe:*

1. Upright and strong plant habit.
2. Dark-colored foliage.
3. Freely and uniformly flowering habit with inflorescences positioned above the foliar plane.
4. Light pink-colored flowers.
5. Long flowering period.
6. Good garden performance.

Plants of the new *Astilbe* differ primarily from plants of the female parent selection in the following characteristics:

1. Plants of the new *Astilbe* have darker-colored developing leaves than plants of the female parent selection.
2. Plants of the new *Astilbe* have darker pink-colored flowers than plants of the female parent selection.

Plants of the new *Astilbe* differ primarily from plants of the male parent, 'Weisse Gloria', in the following characteristics:

1. Plants of the new *Astilbe* have darker-colored developing leaves than plants of 'Weisse Gloria'.
2. Plants of the new *Astilbe* and 'Weisse Gloria' differ in flower color as plants of 'Weisse Gloria' have white-colored flowers.

Plants of the new *Astilbe* can be compared to plants of *Astilbe chinensis* 'Brumalda', not patented. In side-by-side comparisons conducted in Noorden, The Netherlands, plants of the new *Astilbe* differed from plants of 'Brumalda' in the following characteristics:

1. Plants of the new *Astilbe* had darker-colored developing leaves than plants of 'Brumalda'.
2. Plants of the new *Astilbe* and 'Brumalda' differed in flower color as plants of 'Brumalda' had white-colored flowers.

BRIEF DESCRIPTION OF THE PHOTOGRAPHS

The accompanying colored photographs illustrate the overall appearance of the new *Astilbe* plant, showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet comprises a side perspective view of a typical flowering plant of 'Spotlight' grown in a container.

The photograph at the top of the second sheet is a close-up view of typical inflorescences of 'Spotlight'.

The photograph at the bottom of the second sheet is a close-up view of typical leaves of 'Spotlight'.

DETAILED BOTANICAL DESCRIPTION

The aforementioned photographs and following observations, measurements and values describe plants grown in containers in an outdoor nursery in Noorden, The Netherlands, under commercial practice during the summer. During the production of the plants, day temperatures ranging from 12° C. to 30° C. and night temperatures ranging from 5° C. to 15° C. Plants were two years old when the photographs and description were taken. In the following description, color references are made to The Royal Horticultural Society Colour Chart, 2007 Edition, except where general terms of ordinary dictionary significance are used.

Botanical classification: *Astilbe hybrida* 'Spotlight'.

Parentage:

*Female, or seed, parent.*—Unnamed proprietary seedling selection of *Astilbe chinensis*×*Astilbe arendsii*, not patented.

*Male, or pollen, parent.*—*Astilbe arendsii* 'Weisse Gloria', not patented.

Propagation:

*Type.*—By divisions.

*Time to produce a rooted young plant.*—About two months at 18° C. to 20° C.

*Root description.*—Fine, moderately fibrous; brown in color.

*Rooting habit.*—Freely branching; moderately dense.

Plant description:

*Plant form/habit.*—Herbaceous perennial; upright and strong plant habit; roughly narrowly triangular; flowering stems and leaves basal; dense and bushy growth habit; moderately vigorous to vigorous; freely and uniformly flowering with numerous flowers on panicles positioned above the foliar plane.

*Growth rate.*—Moderately fast; from tissue culture plants, about 20 weeks are required to produce fully-grown flowering plants.

*Plant height* (*soil level to top of foliar plane*).—About 38.1 cm.

*Plant height* (*soil level to top of inflorescences*).—About 56.7 cm.

*Plant width* (*spread*).—About 52.9 cm.

*Stem description.*—Length: About 26.9 cm. Diameter: About 3.5 mm. Internode length: About 13.5 cm. Strength: Strong. Texture: Densely pubescent. Color: Close to 144C flushed with close to 176C to 176D.

Foliage description:

*Arrangement.*—Alternate; bipinnate and compound.

*Leaf length* (*excluding petiole*).—About 19.9 cm.

*Leaf width.*—About 18.9 cm.

*Lateral leaflet length.*—About 5.2 cm.

*Lateral leaflet width.*—About 3.4 cm.

*Terminal leaflet length.*—About 7.1 cm.

*Terminal leaflet width.*—About 3.9 cm.

*Lateral and terminal leaflet shape.*—Elliptic.

*Lateral and terminal leaflet apex.*—Acute.

*Lateral and terminal leaflet base.*—Attenuate to rounded.

*Lateral and terminal leaflet margin.*—Biserrate.

*Lateral and terminal leaflet texture, upper and lower surfaces.*—Pubescent, rough.

*Lateral and terminal leaflet venation pattern.*—Pinnate.

*Lateral and terminal leaflet color.*—Developing leaves, upper surface: Between 177A and N199B. Developing leaves, upper surface: Between 177A and 200D.

*Fully expanded leaves, upper surface.*—Between 143A and 146A; margins tinged with close to 183B to 183C; venation, close to 183B.

*Fully expanded leaves, lower surface.*—Close to 146B; margins tinged with close to 183B to 183C; venation, close to 183B to 183C.

*Leaf petiole length.*—About 13 cm.

*Leaf petiole diameter.*—About 2 mm.

*Leaflet petiole length.*—About 4 cm.

*Leaflet petiole width.*—About 2 mm.

*Leaf and leaflet petiole texture, upper and lower surfaces.*—Smooth, glabrous.

*Leaf and leaflet petiole color, upper and lower surfaces.*—Close to 144C flushed with close to 176C to 176D.

Flower description:

*Flower type/habit.*—Numerous single rotate flowers arranged on terminal panicles; flowers fact upright, outward or downward depending on position on the panicle; panicles narrowly triangular in shape; freely and uniformly flowering habit with about 1,250 flowers per inflorescence.

*Fragrance.*—Faintly fragrant; moderately sweet.

*Natural flowering season.*—Long flowering period, plants continuously flower during the summer until the late summer in The Netherlands.

*Postproduction longevity.*—Flowers last about ten days on the plant; flowers persistent.

*Flower buds.*—Height: About 2 mm. Diameter: About 1.5 mm. Shape: Broadly elliptical. Color: Close to 146D; towards the apex, flushed with close to 186A to 186B.

*Inflorescence height.*—About 27.1 cm.

*Inflorescence diameter.*—About 16 cm.

*Flower diameter.*—About 7 mm.

*Flower depth.*—About 5 mm.

*Petals.*—Quantity per flower: Typically five in a single whorl. Length: About 4 mm. Lobe width: About 0.5 mm. Shape: Narrowly lanceolate. Apex: Acute. Margin: Entire. Texture, upper and lower surfaces: Smooth, glabrous. Color: Developing petals, upper and lower surfaces: Between 62D and 69A. Fully expanded petals, upper and lower surfaces: Close to 69B to 69D; color becoming closer to 69D with development.

*Sepals.*—Quantity per flower: Typically five in a single whorl, fused towards the base; calyx campanulate in shape. Length: About 2 mm. Width: About 1 mm. Shape: Broadly ovate. Apex: Acute. Base: Cuneate, fused. Margin: Entire. Texture, upper and lower surfaces: Smooth, glabrous. Color: Developing sepals, upper and lower surfaces: Between 155A and 196D heavily flushed with between 63B and 186A. Fully developed sepals, upper and lower surfaces: Between 155A and 196D.

*Peduncles.*—Length: About 29.1 cm. Diameter: About 2 mm. Angle: Erect to about 5° from vertical. Strength: Strong. Texture: Smooth, glabrous. Color: Close to 182B to 182C.

*Pedicels.*—Length: About 0.5 mm. Diameter: About 0.5 mm. Angle: About 60° from vertical. Strength: Moderately strong. Texture: Smooth, glabrous. Color: Between 155A to 196D flushed with between 63B and 186A.

*Reproductive organs.*—Stamens: Quantity per flower: Typically ten; anthers basifixed. Filament length: About 2 mm. Anther shape: Ovate. Anther length: About 0.5 mm. Anther color: Close to 160D. Pollen amount: Scarce. Pollen color: Close to 4C to 4D. Pistils: Quantity per flower: Two. Pistil length: About 2.5 mm. Style length: About 2 mm. Style color: Close to 64C. Stigma shape: Club-shaped. Stigma color: Close to 64B. Ovary color: Close to 64C to 64D.

*Seed/fruit.*—Seed and fruit development have not been observed.

Disease/pest resistance: Plants of the new *Astilbe* have not been noted to be resistant to pathogens and pests common to *Astilbe.*

Garden performance: Plants of the new *Astilbe* have been observed to have good garden performance and tolerate rain, wind and high temperatures of about 35° C.; plants of the new *Astilbe* have been observed to be hardy to USDA Zone 5.

It is claimed:

1. A new and distinct *Astilbe* plant named 'Spotlight' as illustrated and described.

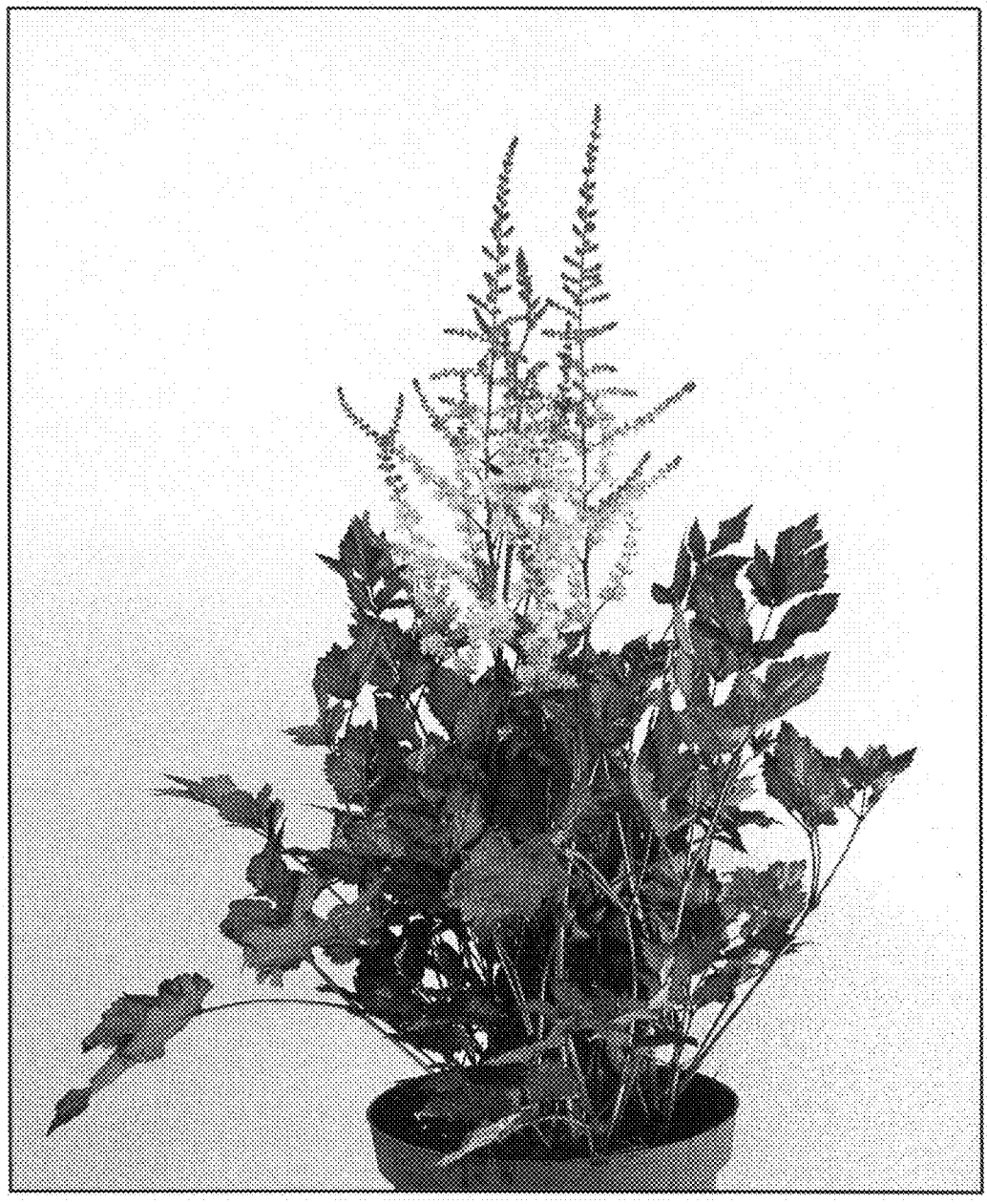

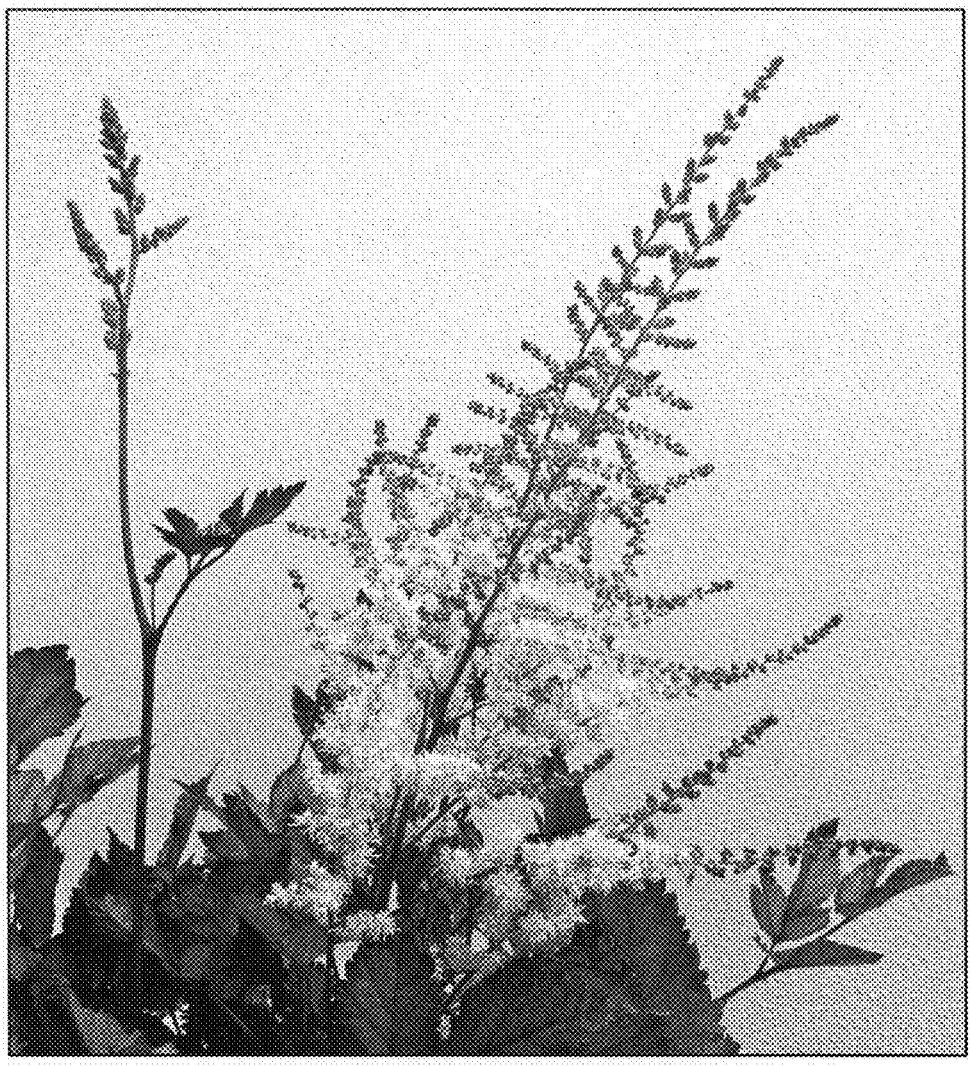
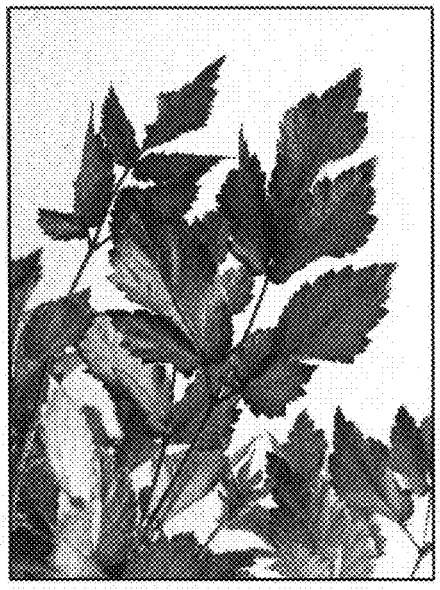

* * * * *